(12) United States Patent
Abo et al.

(10) Patent No.: US 9,593,352 B2
(45) Date of Patent: Mar. 14, 2017

(54) PRODUCTION OF FATTY ACID ALKYL ESTERS BY USE OF TWO LIPOLYTIC ENZYMES

(75) Inventors: Masnobu Abo, Chiba-ken (JP); Morten Wurtz Christensen, Raleigh, NC (US); Zhengyu Hu, Beijing (CN)

(73) Assignee: Novozymes A/S, Bagsvaerd (DK)

( * ) Notice: Subject to any disclaimer, the term of this patent is extended or adjusted under 35 U.S.C. 154(b) by 339 days.

(21) Appl. No.: 13/096,448

(22) Filed: Apr. 28, 2011

(65) Prior Publication Data

US 2011/0201066 A1    Aug. 18, 2011

Related U.S. Application Data

(63) Continuation of application No. 11/813,121, filed as application No. PCT/DK2006/000016 on Jan. 10, 2006, now abandoned.

(60) Provisional application No. 60/643,414, filed on Jan. 12, 2005.

(30) Foreign Application Priority Data

Jan. 10, 2005    (DK) .................................. 2005 00041

(51) Int. Cl.
*C12P 7/64*    (2006.01)
(52) U.S. Cl.
CPC ............... *C12P 7/649* (2013.01); *Y02E 50/13* (2013.01)
(58) Field of Classification Search
None
See application file for complete search history.

(56) References Cited

U.S. PATENT DOCUMENTS

| | | | |
|---|---|---|---|
| 4,056,442 A | 11/1977 | Huang et al. | |
| 5,288,619 A | 2/1994 | Brown et al. | |
| 5,713,965 A | 2/1998 | Foglia et al. | |
| 5,827,719 A | 10/1998 | Sandal et al. | |
| 7,473,539 B2 | 1/2009 | Chou | |
| 2008/0038804 A1 | 2/2008 | Du et al. | |

FOREIGN PATENT DOCUMENTS

| | | |
|---|---|---|
| EP | 0 407 959 | 1/1991 |
| EP | 1 705 238 | 9/2006 |
| JP | 60-234588 | 11/1985 |
| WO | WO/88/02775 | 4/1988 |
| WO | 96/13580 A1 | 5/1996 |

OTHER PUBLICATIONS

Carvalho et al., Biotechnology and Bioengineering, vol. 66, Issue 1, Nov. 1999, pp. 17-34.*
Boutur et al, J Biotechnol, vol. 42, pp. 23-33 (1995).
Du et al, Biotechnol Appl Biochem, vol. 38, pp. 103-106 (2003).
Du et al, Database accession No. 2005-630178 XP-002403032 (2005).
Kaieda et al, J Biosci Bioeng, vol. 91, pp. 12-15 (2001).
Kolattukudy et al, Lipases, pp. 471-504 (1984).
Shimada et al, J Mol CatalB Enzym, vol. 17, pp. 133-142 (2002).
Xu et al, Biocatal Biotransform, vol. 22, pp. 45-48 (2004).
Danieli et al, J Mol Catal B Enzym, vol. 3, pp. 193-201 (1997).
Dormo et al, Biochem Eng J, vol. 21, pp. 229-234 (2004).
Hong Wu, Prepr Rap Am Chem Soc Div Fuel Chem, vol. 48, No. 2, pp. 533-534 (2003).
Samukawa et al, J Biosci Bioeng, vol. 90, No. 2, pp. 180-183 (2000).
Du et al, Accension No. 2005-630178, XP-002403032 of WO2005075615—2 pages (2005).

* cited by examiner

*Primary Examiner* — Irene Marx
(74) *Attorney, Agent, or Firm* — Kristin McNamara

(57) ABSTRACT

A method for producing fatty acid alkyl esters, wherein a solution comprising triglyceride and alcohol is contacted with a first lipolytic enzyme having a relatively higher activity on free fatty acids than on triglyceride and a second lipolytic enzyme having a relatively higher activity on triglyceride than on free fatty acids.

14 Claims, No Drawings

PRODUCTION OF FATTY ACID ALKYL ESTERS BY USE OF TWO LIPOLYTIC ENZYMES

CROSS-REFERENCE TO RELATED APPLICATIONS

This application is a continuation of U.S. application Ser. No. 11/813,121 filed on Jun. 29, 2007 (abandoned), which is a 35 U.S.C. 371 national application of PCT/DK2006/000016 filed Jan. 10, 2006, which claims priority or the benefit under 35 U.S.C. 119 of Danish application no. PA 2005 00041 filed Jan. 10, 2005 and U.S. provisional application No. 60/643,414 filed Jan. 12, 2005, the contents of which are fully incorporated herein by reference.

FIELD OF THE INVENTION

The present invention relates to a method for producing fatty acid alkyl esters from triglyceride by use of a first lipolytic enzyme which favours the conversion of triglyceride to fatty acid alkyl esters and a second lipolytic enzyme which favours the conversion of free fatty acids to fatty acid alkyl esters.

BACKGROUND ART

Biodiesel, generally classified as mono-alkyl esters of fats and oils, has become more attractive recently because of its environmental benefits. Although biodiesel is at present successfully produced chemically (using e.g. NaOH and/or sodium methoxide as catalyst), there are several associated problems to restrict its development, such as pre-processing of oil due to high contents of free fatty acids, removal of chemical catalyst from ester and glycerol phase and removal of inorganic salts during glycerol recovery.

The disadvantages caused by chemical catalysts are largely prevented by using lipolytic enzymes as the catalysts and in recent years interest has developed in the use of lipases with or without immobilization in transesterification for the production of biodiesel.

Fungal esterases may be used in the enzymatic production of esters, where they may replace catalysts like mineral acid (e.g. sulphuric acid, hydrogen chloride, and chlorosulfonic acid), amphoteric hydroxides of metals of groups I, II, III, and IV, and others. The use of enzymes for ester synthesis has been described in the prior art, in particular enzymes classified in EC 3.1.1 Carboxylic ester hydrolases according to Enzyme Nomenclature (Recommendations of the Nomenclature Committee of the International Union of Biochemistry and Molecular Biology, 1992 or later).

WO 88/02775 discloses lipases A and B from *Candida antarctica*. It states that *C. antarctica* lipase B (CALB) is more effective for ester synthesis.

Cutinases are lipolytic enzymes capable of hydrolyzing the substrate cutin. Cutinases are known from various fungi (P. E. Kolattukudy in "Lipases", Ed. B. Borgström and H. L. Brockman, Elsevier 1984, 471-504). The amino acid sequence of a cutinase from *Humicola insolens* has been published (U.S. Pat. No. 5,827,719).

Many researchers have reported that a high yield of alkyl esters could be reached in the presence of organic solvents, but because of the toxicity and flammability of organic solvents lipase-catalysed alcoholysis in a solvent-free medium is more desirable. Methanolysis catalysed by lipases has been shown to take place in a water-containing system free of organic solvents. In such systems lipases which are less sensitive to methanol is advantageous (Kaieda et al. J. Biosci. Bioeng. 2001, 91:12-15). It is well known that excessive short-chain alcohols such as methanol might inactivate lipase seriously. However, at least three molar equivalents of methanol are required for the complete conversion of the oil to its corresponding methyl ester. Du et al. (Biotechnol. Appl. Biochem. 2003, 38:103-106) studied the effect of molar ratio of oil/methanol comparatively during non-continuous batch and continuous batch operation.

To avoid inactivation of the lipases the methanol concentration has been kept low by step-wise addition of methanol throughout the reaction (Shimada et al. J Mol. Catalysis Enzymatic, 2002, 17:133-142; Xu et al. 2004, Biocat. Biotransform. 22:45-48).

Boutur et al. (J. Biotechnol. 1995, 42:23-33) reported a lipase from *Candida deformans* which were able to catalyse both alcoholysis of triglyceride (TG) and esterification of free fatty acids (FFA), but not under the same reaction conditions. Under the conditions described by Boutur et al. only the esterification was catalysed.

In order to obtain a more economic production of fatty acid ethyl esters for biodiesel, there is a need for a faster conversion of fats and oils to their corresponding methyl esters and a higher yield in said conversion.

SUMMARY OF THE INVENTION

The present invention relates to a method for producing fatty acid alkyl esters, such as fatty acid methyl esters (FAME) and fatty acid ethyl esters. Such esters are also called biodiesel, because they are used as an additive to mineral diesel to result in a sulphur-free, higher-cetane-number fuel, which is partly based on renewable resources.

The method of the invention includes a solution comprising alcohol, triglyceride and/or free fatty acids, which solution is contacted with a first lipolytic enzyme and a second lipolytic enzyme of different specificity, wherein the lipolytic enzymes catalyse the conversion of triglyceride or free fatty acids or a mixture of both to fatty acid alkyl esters. The first lipolytic enzyme is characterised in that it exhibits higher activity against triglyceride than free fatty acids, whereas the second lipolytic enzyme exhibits higher activity against free fatty acids than triglyceride. The activity of the first and second lipolytic enzymes is determined by use of the methods described in Example 1 and 2 below.

The first lipolytic enzyme is defined as one having a ratio of activity on TG/activity on FFA below 0.2. The second lipolytic enzyme is defined as one having a ratio of activity on TG/activity on FFA above 0.5.

The combination of a first lipolytic enzyme and a second lipolytic enzyme according to the present invention results in a synergistic effect on the conversion of triglyceride and triglyceride in combination with free fatty acids to fatty acid alkyl esters, whereby a higher percentage of conversion is obtained in a shorter period of time.

Further, the invention relates to a batch process or a continuous, staged process to produce fatty acid alkyl esters using a first and a second lipolytic enzyme as described above, wherein the alcohol is added continuously or step-wise, and wherein the enzymes are recycled or used only once.

DETAILED DESCRIPTION OF THE INVENTION

The present invention relates to a method for producing fatty acid alkyl esters. The method of the invention includes a solution comprising alcohol, and a substrate, which comprises triglyceride and/or free fatty acids. The solution is contacted with a first lipolytic enzyme and a second lipolytic enzyme of different specificity, wherein the lipolytic enzymes catalyse the conversion of triglyceride or free fatty acids or a mixture of both to fatty acid alkyl esters.

Substrates

Suitable substrates for production of fatty acid alkyl esters in accordance with the present invention are a broad variety of vegetable oils and fats; rapeseed and soybean oils are most commonly used, though other crops such as mustard, sunflower, canola, coconut, hemp, palm oil and even algae show promise. The substrate can be of crude quality or further processed (refined, bleached and deodorized). Also animal fats including tallow, lard, poultry, marine oil as well as waste vegetable and animal fats and oil, commonly known as yellow and brown grease can be used. The suitable fats and oils may be pure triglyceride or a mixture of triglyceride and free fatty acids, commonly seen in waste vegetable oil and animal fats. The substrate may also be obtained from vegetable oil deodorizer distillates. The type of fatty acids in the substrate comprises those naturally occurring as glycerides in vegetable and animal fats and oils. These include oleic acid, linoleic acid, linolenic acid, palmetic acid and lauric acid to name a few. Minor constituents in crude vegetable oils are typically phospholipids, free fatty acids and partial glycerides i.e. mono- and diglycerides. When used herein the phrase "fatty acid residues" refers to fatty acids, either free or esterified as in triglycerides, diglycerides, monoglycerides or fatty acid alkyl esters.

Biodiesel

Fatty acid alkyl esters, such as fatty acid methyl esters (FAME) and fatty acid ethyl esters are also called biodiesel, because they are used as an additive to fossil diesel. Biodiesel constitutes an increasingly important additive or substitute for diesel fuels based on fossil oil because it is produced from renewable resources.

Alcohol

The alcohol used in the method of the invention is preferably a lower alcohol having 1 to 5 carbon atoms ($C_1$-$C_5$). Preferred alcohols are methanol and ethanol.

Lipolytic Enzyme

The first lipolytic enzyme according to the present invention is characterised in that it exhibits higher activity against triglyceride than free fatty acids, whereas the second lipolytic enzyme exhibits higher activity against free fatty acids than triglyceride. The activity of the lipolytic enzymes against triglycerides and free fatty acid is determined as described in Example 1 and Example 2, respectively.

According to the present invention, the first lipolytic enzyme is defined as one having a ratio of activity on triglyceride (measured as conversion of triglyceride to fatty acid alkyl esters) to activity on FFA (measured as conversion of FFA to fatty acid alkyl esters) below 0.2. The second lipolytic enzyme is defined as one having a ratio of activity on triglyceride (measured as conversion of triglyceride to fatty acid alkyl esters) to activity on FFA (measured as conversion of FFA to fatty acid alkyl esters) above 0.5.

Accordingly, the present invention relates to a method for producing fatty acid alkyl esters, characterised in that a solution comprising triglyceride and alcohol is contacted with a first lipolytic enzyme having a ratio of activity on triglyceride to activity on FFA below 0.2 and a second lipolytic enzyme having a ratio of activity on triglyceride to activity on FFA above 0.5.

The first lipolytic enzyme preferably has a ratio of activity on triglyceride to activity on FFA in the range of 0.01-0.2, more preferably in the range of 0.01-0.1, more preferably in the range of 0.0125-0.05, more preferably in the range of 0.015-0.025, even more preferably in the range of 0.02-0.024. The second lipolytic enzyme preferably has a ratio of activity on triglyceride to activity on FFA in the range of 0.5-20, more preferably in the range of 0.6-10, more preferably in the range of 0.7-5, even more preferably in the range of 0.8-1.5.

As stated above, the activity of the lipolytic enzymes against triglycerides and free fatty acid is determined as described in Example 1 and Example 2, respectively. Below, the ratio of activity on triglyceride (abbreviated TG) as measured in Example 1 to activity on free fatty acids (abbreviated FFA) as measured in Example 2, has been calculated for the tested lipolytic enzymes:

CALB: TG/FFA=0.55/26.41=0.021

*H. insolens* cutinase: TG/FFA=12.13/10=1.213

*T. lanuginosus* lipase: TG/FFA=13.22/16.25=0.814.

The combination of a first lipolytic enzyme and a second lipolytic enzyme according to the present invention results in a synergistic effect on the conversion of triglyceride and/or free fatty acids to fatty acid alkyl esters, whereby a higher percentage of conversion is obtained in a shorter period of time.

In a preferred embodiment of the method of the present invention a first lipolytic enzyme of the present invention is lipase B from *Candida antarctica* (CALB) as disclosed in WO 88/02775, whereas the second lipolytic enzyme is one of the *Thermomyces lanuginosus* (previously *Humicola lanuginosus*) lipase variants exemplified in WO 00/60063 and the *Humicola insolens* cutinase variants disclosed in Example 2 of WO 01/92502, hereinafter referred to as *T. lanuginosus* lipase and *H. insolens* cutinase respectively. In a second preferred embodiment a first lipolytic enzyme includes *Hyphozyma* sp. lipase and *Candida parapsilosis* lipase, whereas a second lipolytic enzyme of the present invention includes *C. antarctica* lipase A as disclosed in WO 88/02775 and lipases from *Humicola lanuginosus* (EP 258 068), *Candida rugosa, Pseudomonas cepacia, Geotrichum candidum, Rhizomucor miehei, Cryptococcus* spp. S-2 and *Candida parapsilosis*.

In a third embodiment the first lipolytic enzyme is homologous with CALB, *Hyphozyma* sp. lipase or *Candida parapsilosis* lipase, whereas the second lipolytic enzyme is homologous with *T. lanuginosus* lipase, *H. insolens* cutinase or any of the lipases from *Humicola lanuginosus* (EP 258 068), *Candida rugosa, Pseudomonas cepacia, Geotrichum candidum, Rhizomucor miehei, Cryptococcus* spp. S-2 and *Candida parapsilosis*.

Preferably, the first lipolytic enzyme according to the method of the present invention is 60% identical with CALB, whereas the second lipolytic enzyme is 60% identical with the *T. lanuginosus* lipase, the *H. insolens* cutinase. More preferably the first lipolytic enzyme is 70% identical with CALB, even more preferably the first lipolytic enzyme is 75%, 80%, 85%, 88%, 90%, 92%, 94%, 95%, 96%, 97%, 98% or even 99% identical with CALB. Similarly, the second lipolytic enzyme is preferably 70% identical with *T. lanuginosus* lipase and *H. insolens* cutinase, more preferably the second lipolytic enzyme is 75%, 80%, 85%, 88%, 90%, 92%, 94%, 95%, 96%, 97%, 98% or even 99% identical with *T. lanuginosus* lipase or *H. insolens* cutinase.

The enzymes may be applied as lyophilised powder, immobilised or in aqueous solution.

For purposes of the present invention, the degree of identity may be suitably determined according to the method described in Needleman, S. B. and Wunsch, C. D., (1970), Journal of Molecular Biology, 48, 443-45, with the following settings for polypeptide sequence comparison: GAP creation penalty of 3.0 and GAP extension penalty of 0.1. The determination may be done by means of a computer program known such as GAP provided in the GCG program package (Program Manual for the Wisconsin Package, Version 8, August 1994, Genetics Computer Group, 575 Science Drive, Madison, Wis., USA 53711).

Two given sequences can be aligned according to the method described in Needleman (supra) using the same parameters. This may be done by means of the GAP program (supra).

Further, the invention relates to a batch process and/or a continuous, staged process to produce fatty acid alkyl esters using a first and a second lipolytic enzyme as described above, wherein the alcohol is added continuously or stepwise, and wherein the enzymes are recycled or used only once. If the enzymes are in an aqueous phase, this phase can be separated from the fatty phase by a decanter, a settler or by centrifugation. In the continuously process the two phases, oil and aqueous, respectively, can be processed counter-currently. Kosugi, Y; Tanaka, H. and Tomizuka, (1990), Biotechnology and Bioengineering, vol. 36, 617-622, describes a continuous, counter-current process to hydrolyse vegetable oil by immobilized lipase.

General Description of Preparation of Fatty Acid Alkyl Esters

The substrate comprising triglyceride is mixed with alcohol, preferably methanol or ethanol and heated to 30-60° C., preferably 50° C. on a reciprocal water shaking bath (200 rpm). Preferably water is added and the solution is mixed and further heated to the desired temperature. The enzymes are added and the solution is mixed vigorously and left on reciprocal water shaking bath at the desired temperature, preferably 50° C. and 200 rpm to react. The phases of the reaction mixture can be mixed by the use of high shear mixers, such as types from Silverson or IKA Labortechnik, as used in enzymatic degumming of vegetable oil (Clausen, K. (2001), European Journal of Lipid Science and Technology, vol. 103, 333-340).

The [methanol]/[fatty acid residue] molar ratio should be at least 0.1 and maximum 10, preferable in the range 0.3-5, more preferable 0.4-2. The alcohol can be added stepwise to the reaction over time. Water can be added separately or within an aqueous enzyme solution. The final concentration of water in the reaction mixture can be 0-50% (w/w), preferably 5-40%, more preferably 5-30%. The substrate comprises 1-99% (w/w) triglyceride, preferably in the range of 70-95%. Further, the substrate may comprise free fatty acids amounting to 0.01-95% (w/w), preferably in the range of 0.01-30%. Also, mono- and diglycerides and phospholipids may be present.

The course of the reaction can be followed by withdrawing samples from the reaction mixture after a certain period of reaction time. The samples are centrifuged for 14 minutes at 14000 rpm. The upper layer consists of fatty material not soluble in the water phase and this is analyzed by $^1$H NMR (using $CDCl_3$ as solvent). After the reaction has ended the glycerol phase is removed either by decanting or centrifugation.

Cloning a DNA Sequence Encoding a Lipolytic Enzyme

The DNA sequence encoding a parent lipolytic enzyme may be isolated from any cell or microorganism producing the lipolytic enzyme in question, using various methods well known in the art. First, a genomic DNA and/or cDNA library should be constructed using chromosomal DNA or messenger RNA from the organism that produces the lipolytic enzyme to be studied. Then, if the amino acid sequence of the lipolytic enzyme is known, labeled oligonucleotide probes may be synthesized and used to identify lipolytic enzyme-encoding clones from a genomic library prepared from the organism in question. Alternatively, a labeled oligonucleotide probe containing sequences homologous to another known lipolytic enzyme gene could be used as a probe to identify lipolytic enzyme-encoding clones, using hybridization and washing conditions of lower stringency.

Yet another method for identifying lipolytic enzyme-encoding clones would involve inserting fragments of genomic DNA into an expression vector, such as a plasmid, transforming cutinase-negative bacteria with the resulting genomic DNA library, and then plating the transformed bacteria onto agar containing a substrate for lipolytic enzyme (i.e. triglyceride), thereby allowing clones expressing the lipolytic enzyme to be identified.

Alternatively, the DNA sequence encoding the enzyme may be prepared synthetically by established standard methods, e.g. the phosphoroamidite method described by S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487-491.

Expression Vector

The recombinant expression vector carrying the DNA sequence encoding a lipolytic enzyme of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

The expression vector of the invention may also comprise a suitable transcription terminator and, in eukaryotes, polyadenylation sequences operably connected to the DNA sequence encoding the lipolytic enzyme of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a cutinase variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a lipolytic enzyme of the invention, especially in a bacterial host, are the promoter of the lac operon of *E. coli*, the *Streptomyces coelicolor* agarase gene dagA promoters, the promoters of the *Bacillus licheniformis* alfa-amylase gene (amyL), the promoters of the *Bacillus stearothermophilus* maltogenic amylase gene (amyM), the promoters of the *Bacillus amyloliquefaciens* alfa-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizomucor miehei* aspartic proteinase, *A. niger* neutral alfa-amylase, *A. niger* acid stable alfa-amylase, *A. niger* glucoamylase, *Rhizomucor miehei* lipase, *A. oryzae* alkaline protease, *A. oryzae* triose phosphate isomerase, or *A. nidulans* acetamidase.

Host Cells

The cell of the invention, either comprising a DNA construct or an expression vector of the invention as defined above, is advantageously used as a host cell in the recombinant production of a lipolytic enzyme of the invention. The cell may be transformed with the DNA construct of the invention encoding the lipolytic enzyme, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, particularly a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gram negative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*.

The host cell may also be a filamentous fungus e.g. a strain belonging to a species of *Aspergillus*, particularly *Aspergillus oryzae* or *Aspergillus niger*, or a strain of *Fusarium*, such as a strain of *Fusarium oxysporum, Fusarium graminearum* (in the perfect state named *Gibberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucinum, Fusarium roseum*, and *Fusarium roseum* var. *graminearum*), *Fusarium cerealis* (synonym with *Fusarium crokkwellense*), or *Fusarium venenatum*.

In a particular embodiment of the invention the host cell is a protease deficient or protease minus strain. This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host microorganism is described in EP 238 023 (Novo Nordisk A/S), the contents of which are hereby incorporated by reference.

Production of Lipolytic Enzyme by Cultivation of Transformant

The invention relates, inter alia, to a method of producing a lipolytic enzyme of the invention, which method comprises cultivating a host cell under conditions conducive to the production of the lipolytic enzyme and recovering the lipolytic enzyme from the cells and/or culture medium.

The medium used to cultivate the cells may be any conventional medium suitable for growing the host cell in question and obtaining expression of the lipolytic enzyme of the invention. Suitable media are available from commercial suppliers or may be prepared according to published recipes (e.g. as described in catalogues of the American Type Culture Collection).

The lipolytic enzyme secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Materials and Methods

Lipase Activity on Tributyrin (LU)

A substrate for lipolytic enzymes is prepared by emulsifying tributyrin (glycerin tributyrate) using gum Arabic as emulsifier. The hydrolysis of tributyrin at 30° C. at pH 7 is followed in a pH-stat titration experiment. One unit of lipase activity (1 LU) equals the amount of enzyme capable of releasing 1 µmol butyric acid/min at the standard conditions.

Preparation of Fatty Acid Alkyl Ester 8.00 gram of substrate is mixed with methanol (0.500 ml=>0.395 gram). The following types of substrates were used:

Example 1) 100% salad oil (refined, bleached and deodorized soybean oil, RBD SBO);
Example 2) 100% oleic acid;
Example 3) mixture of 20% w/w oleic acid in RBD SBO The substrate-methanol mixture is heated to 50° C. on a reciprocal water shaking bath (200 rpm). Demineralised water is added (volume depending on added enzyme volume; total amount of water: 4.00 ml including water from enzyme addition), corresponding to 32 w/w % of the total mixture. The mixture is heated to 50° C. Then enzyme is added to the mixture and vigorously mixed for 10 sec. and left on reciprocal water shaking bath at 50° C. and 200 rpm. The phases of the reaction mixture can be mixed by the use of high shear mixers, such as types from Silverson Ltd. UK or IKA Kunkel.

Samples are withdrawn from the reaction mixture after 3 hrs. reaction time and centrifuged for 14 minutes at 14000 rpm. The upper layer consists of fatty material not soluble in the water phase and this is analyzed by $^1$H NMR (using $CDCl_3$ as solvent) Varian 400 MHz spectrometer (Varian Inc. CA, USA). The conversion of the fatty acids residues into fatty acid methyl ester is determined by the ratio of the methyl signals from the fatty acid methyl esters, —COOC$\underline{H}_3$ (3.70 ppm) and C$\underline{H}_3$CH$_2$— (1.0-0.9 ppm) from the fatty acid residues.

The enzyme dose is based on a total 0.4 mg protein/8.00 gram substrate. For testing a synergistic effect of two enzymes combined; 0.2 mg of each enzyme were added to 8 gram of substrate and compared to the each of the single enzymes at a dose of 0.4 mg/8 gram of substrate. To relate the amount of protein to an enzyme activity, a standard enzyme activity assay can be applied, in this case the LU-assay as described above (lipase activity on tributyrine). The following enzyme preparations were tested:
1. *T. lanuginosus* lipase (TLL, specific activity 7000 LU/mg protein)
2. *C. antarctica* lipase B (CALB, specific activity 500 LU/mg protein)
3. *H. insolens* cutinase (cutinase, specific activity 1800 LU/mg protein)

Enzyme dose and additional water volumes for experiments with single enzymes:
1. TLL: 0.700 ml of a 4000 LU/ml enzyme solution+3.30 ml water
2. CALB: 1.680 ml of a 119 LU/ml enzyme solution+2.32 ml water
3. Cutinase: 0.450 ml of a 1600 LU/ml enzyme solution+3.55 ml water Enzyme dose and additional water volumes for experiments with combination of enzymes:
1. TLL+CALB: (0.350 ml of a 4000 LU/ml TLL solution+0.840 ml of a 119 LU/ml CALB solution+2.810 ml water)
2. Cutinase+CALB: (0.225 ml of a 1600 LU/ml cutinase solution+0.840 ml of a 119 LU/ml CALB solution+2.935 ml water).

EXAMPLES

Example 1

Preparation of Fatty Acid Alkyl Esters from Triglycerides

Refined, bleached and deodorized soybean oil (RBD SBO, salad oil) was used as substrate according to the general method described above.

The conversions (%) of fatty acid residues into FAME after 3 hours reaction time using different lipolytic enzymes are shown in Table 1, whereas the conversion (%) achieved with a combination of CALB and TLL is shown in Table 2. Coefficient of Variation in % (CV %) of four identical experiments was determined to be 2.2%.

TABLE 1

| Single enzymes, % conversion of fatty acid residues into FAME | |
|---|---|
| CALB | 0.55 |
| Cutinase | 12.13 |
| TLL | 13.22 |

TABLE 2

| Combination of enzymes, % conversion of fatty acid residues into FAME. | |
|---|---|
| CALB + TLL | 16.21 |

Example 2

Preparation of Fatty Acid Alkyl Esters from Oleic Acid

Oleic acid was used as substrate according to the general method described above. The conversions (%) of fatty acid residues into FAME after 3 hours reaction time using different lipolytic enzymes are shown in Table 3.

TABLE 3

| Single enzymes, % conversion of fatty acid residues into FAME. | |
|---|---|
| CALB | 26.41 |
| Cutinase | 10 |
| TLL | 16.25 |

Example 3

Preparation of Fatty Acid Alkyl Esters from Triglyceride Containing Free Fatty Acids A mixture of 20% w/w oleic acid in RBD SBO was used as substrate according to the general method described above. The conversions (%) of fatty acid residues into FAME after 3 hours reaction time using different lipolytic enzymes and combinations of said enzymes are shown in Table 4 and 5.

TABLE 4

| Single enzymes, % conversion of fatty acid residues into FAME. | |
|---|---|
| CALB | 16.58 |
| Cutinase | 11.22 |
| TLL | 14.09 |

TABLE 5

| Combination of enzymes, % conversion of fatty acid residues into FAME. | |
| --- | --- |
| CALB + Cutinase | 18.82 |
| CALB + TLL | 20 |

The invention claimed is:

1. A method for producing fatty acid alkyl esters, comprising reacting (a) a substrate, which substrate comprises triglyceride and free fatty acids (FFA), and (b) an alcohol, which alcohol is a lower alcohol having 1 to 5 carbon atoms, with a first lipolytic enzyme having a ratio of activity on triglyceride to activity on FFA in the range of 0.01-0.2, wherein the first lipolytic enzyme is Lipase B from *Candida Antarctica*, and a second lipolytic enzyme having a ratio of activity on triglyceride to activity on FFA in the range of 0.5-20, wherein the second lipolytic enzyme is a cutinase; thereby producing fatty acid alkyl esters.

2. The method of claim 1, wherein the triglyceride is derived from the group consisting of vegetable oil feedstock, animal fats, and a combination thereof.

3. The method of claim 1, wherein the molar ratio between alcohol and fatty acid residues is at least 0.1 and maximum 10.

4. The method of claim 1, wherein the molar ratio between alcohol and fatty acid residues is in the range 0.3-5.

5. The method of claim 1, wherein the molar ratio between alcohol and fatty acid residues is in the range 0.4-2.

6. The method of claim 1, wherein the alcohol is methanol or ethanol.

7. The method of claim 1, wherein the substrate, alcohol and first lipolytic enzyme and second lipolytic enzyme further comprises water.

8. The method of claim 1, wherein the second lipolytic enzyme is *H. insolens* cutinase.

9. The method of claim 1, which is a batch method.

10. The method of claim 1, which is a continuous method.

11. The method of claim 1, further comprising mixing the substrate, alcohol and first lipolytic enzyme and second lipolytic enzyme using a high shear mixer.

12. The method of claim 1, which is a counter-current process.

13. The method of claim 2, wherein the vegetable oil feedstock is rapeseed oil, soybean oil, mustard oil, sunflower oil, canola oil, coconut oil, hemp oil, palm oil, tall oil, or a combination thereof.

14. The method of claim 2, wherein the animal fat is tallow, lard, poultry fat, fish oil, or a combination thereof.

* * * * *